United States Patent
Shah

(10) Patent No.: US 10,668,273 B2
(45) Date of Patent: Jun. 2, 2020

(54) NEURAL INTERFACES INCLUDING EXTENSIBLE LEAD BODIES

(71) Applicant: Verily Life Sciences LLC, South San Francisco, CA (US)

(72) Inventor: Kedar Shah, San Francisco, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 173 days.

(21) Appl. No.: 15/995,923

(22) Filed: Jun. 1, 2018

(65) Prior Publication Data

US 2018/0345009 A1 Dec. 6, 2018

Related U.S. Application Data

(60) Provisional application No. 62/514,186, filed on Jun. 2, 2017.

(51) Int. Cl.
*A61N 1/05* (2006.01)

(52) U.S. Cl.
CPC ......... *A61N 1/0551* (2013.01); *A61N 1/0529* (2013.01); *A61N 1/0534* (2013.01); *A61N 1/0541* (2013.01)

(58) Field of Classification Search
None
See application file for complete search history.

(56) References Cited

U.S. PATENT DOCUMENTS

| | | |
|---|---|---|
| 8,332,042 B2 | 12/2012 | Williams |
| 8,825,179 B2 | 9/2014 | Walker et al. |
| 2007/0049987 A1 | 3/2007 | Greenberg et al. |
| 2008/0039917 A1 | 2/2008 | Cross et al. |

FOREIGN PATENT DOCUMENTS

| | | |
|---|---|---|
| WO | 2008013730 A1 | 1/2008 |
| WO | 2012154256 A1 | 11/2012 |
| WO | 2016201151 A1 | 12/2016 |

OTHER PUBLICATIONS

International Application No. PCT/US2018/035638, "International Search Report and Written Opinion", dated Nov. 12, 2018, 17 pages.
International Application No. PCT/US2018/035638, "Invitation to Pay Add'l Fees and Partial Search Report", dated Sep. 13, 2018.
International Application No. PCT/US2018/035638, "International Preliminary Report on Patentability", dated Dec. 12, 2019, 11 pages.

*Primary Examiner* — Brian T Gedeon
(74) *Attorney, Agent, or Firm* — Kilpatrick Townsend & Stockton LLP

(57) ABSTRACT

A device is described that includes a neural interface and a lead body. The lead body and the neural interface are formed from a flexible circuit. The flexible circuit includes an exposed electrode. The lead body includes an elongate planar strand that is coiled about a central axis of the lead body. The elongate planar strand includes a conductive trace extending between the exposed electrode and a distal end of the elongate planar strand.

29 Claims, 6 Drawing Sheets

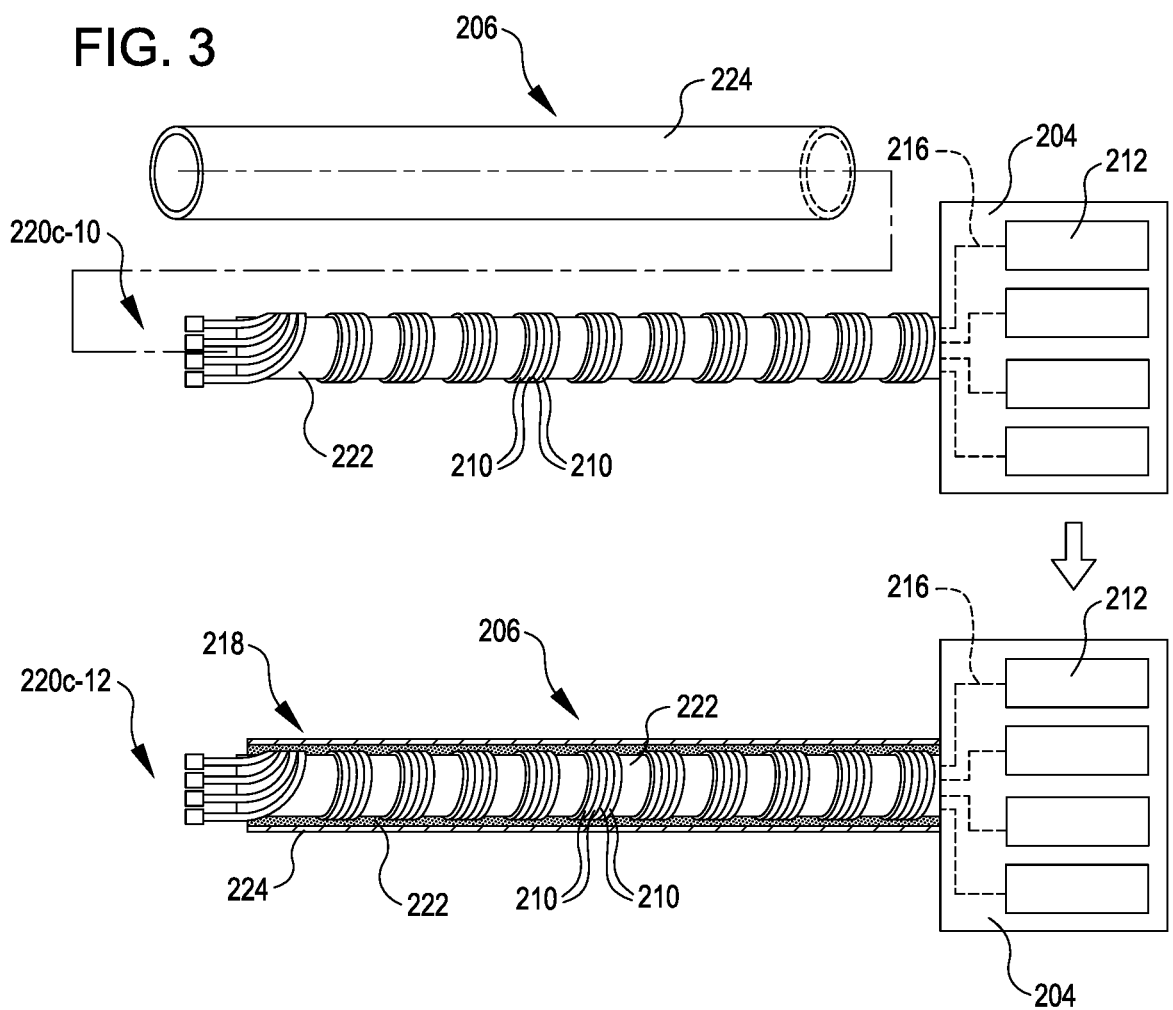

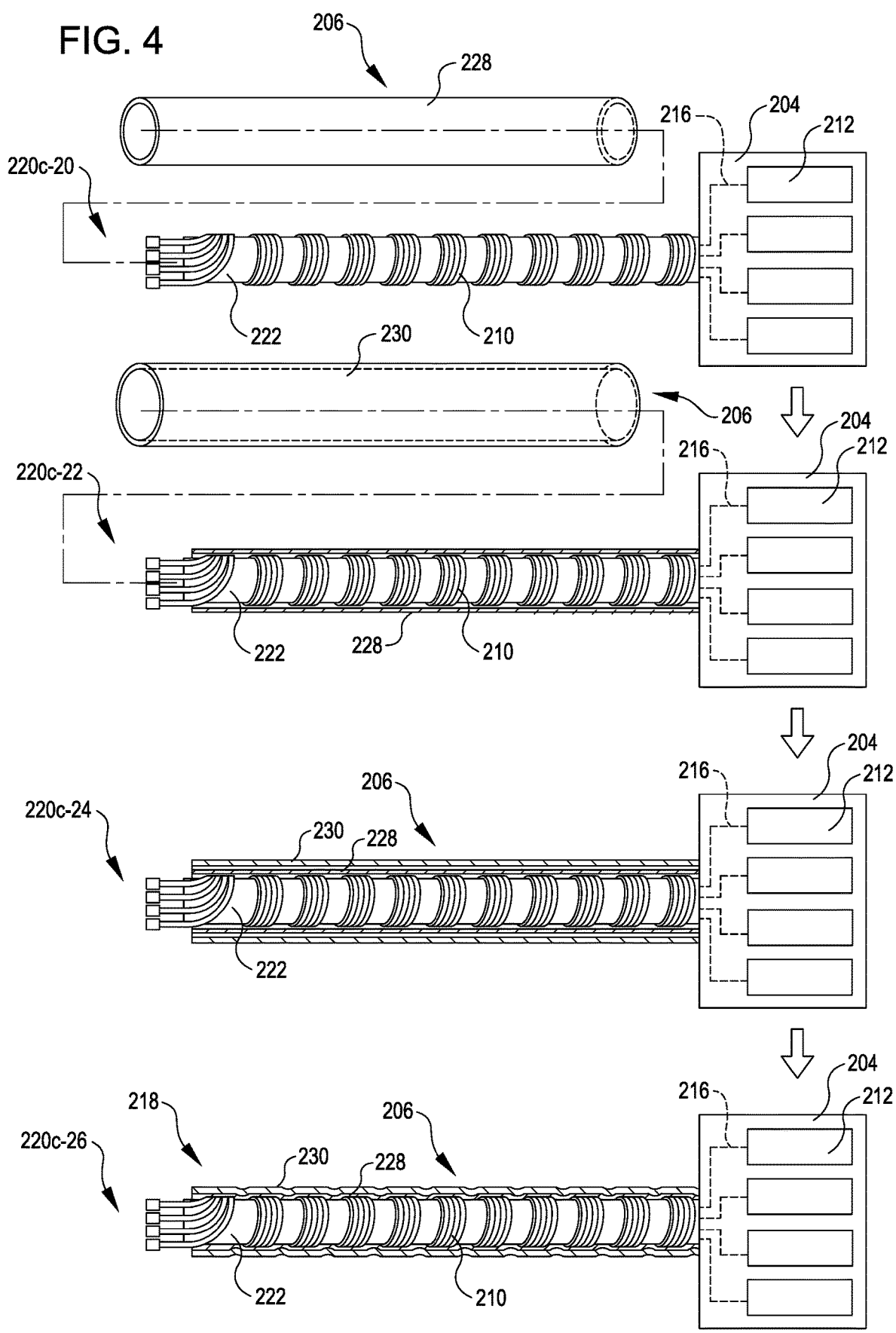

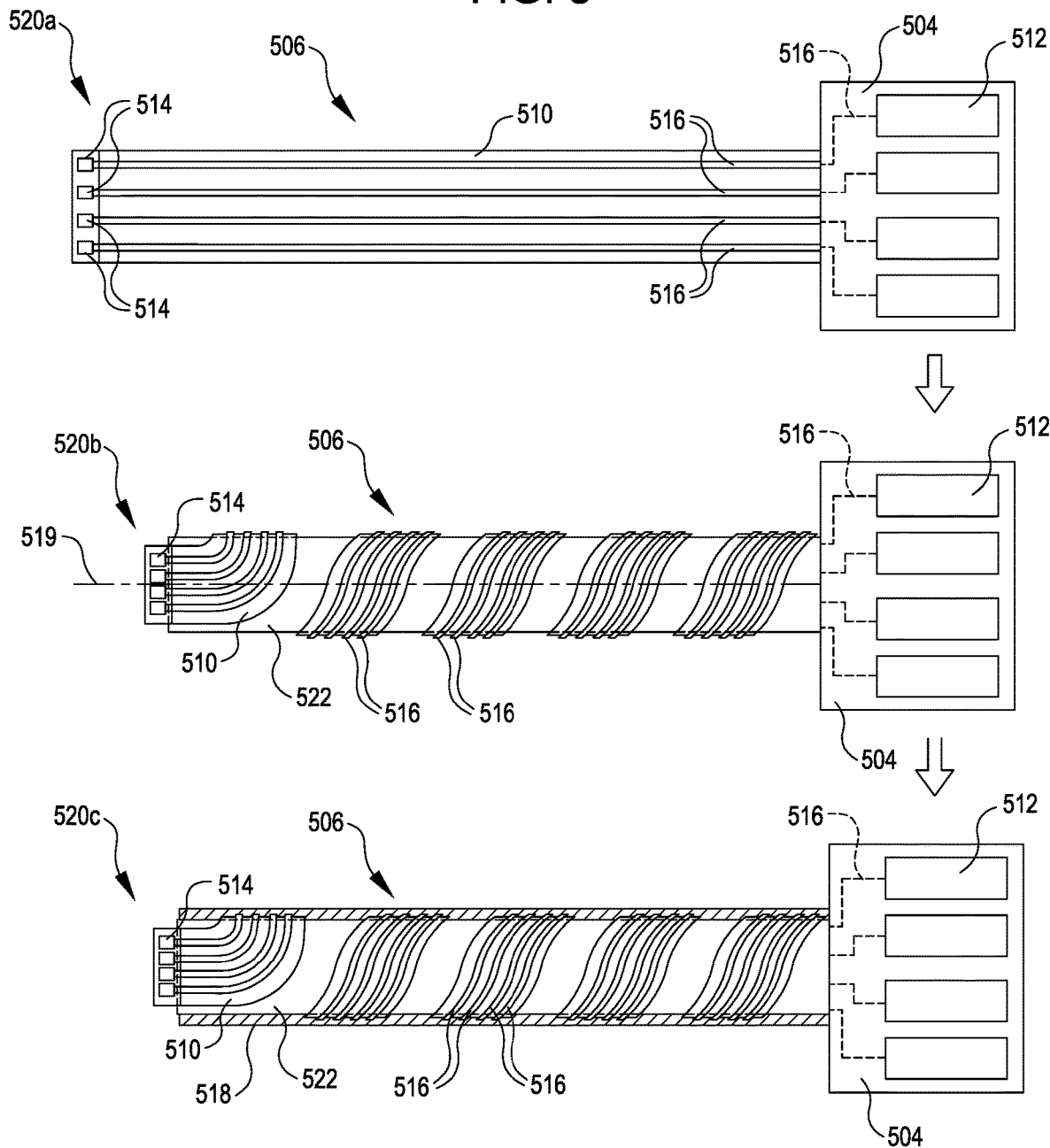

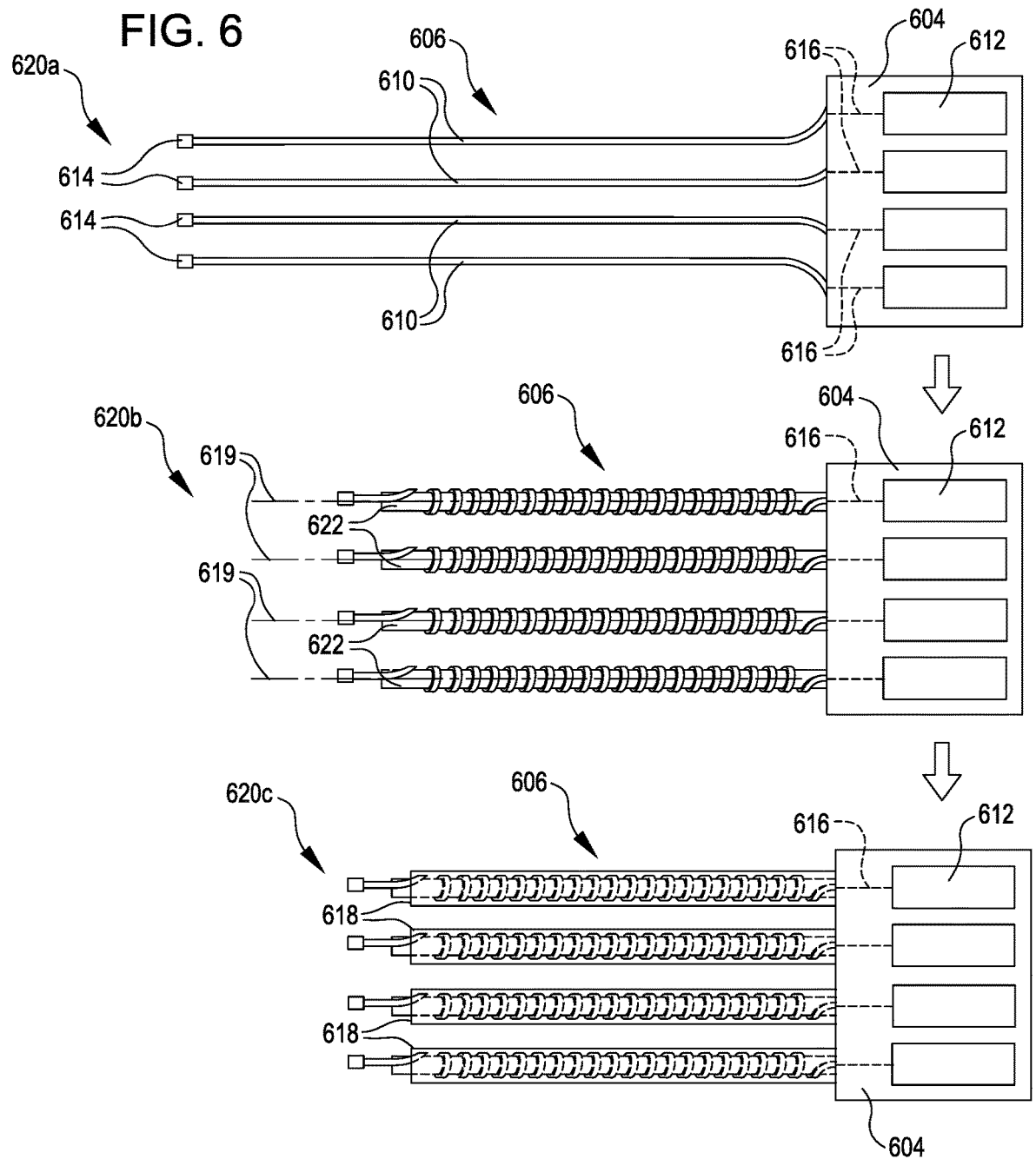

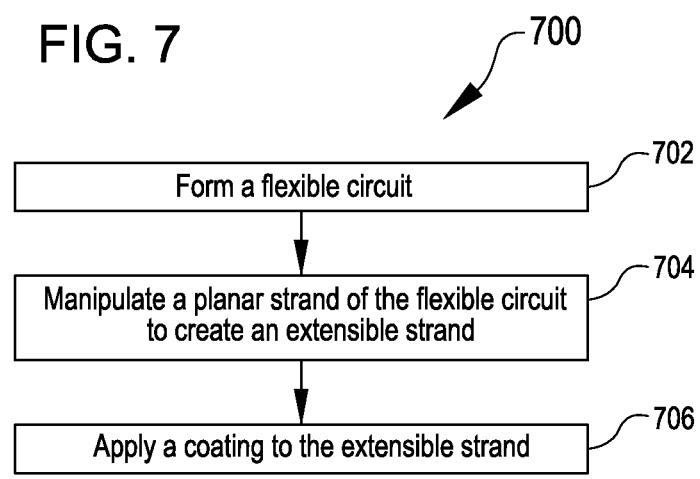

NEURAL INTERFACES INCLUDING EXTENSIBLE LEAD BODIES

CROSS-REFERENCE TO RELATED APPLICATIONS

The present application claims priority to Provisional Application No. 62/514,186, filed on Jun. 2, 2017, and entitled "Neural Interfaces Including Extensible Lead Bodies," the entirety of which is hereby incorporated by reference herein.

BACKGROUND

Implantable medical devices can be used for monitoring (e.g., ongoing glucose monitoring) and for stimulation (e.g., to regulate the beating of a heart). Such devices can include electrodes. The electrodes can be placed at a target location for monitoring or stimulation. In a monitoring scenario, the electrodes gather information from the target location and the electronics package processes the information. In a stimulation scenario, the electronics package generates electrical signals that are delivered to the target location via the electrodes.

The electrodes can be connected to the electronics package via lead bodies formed from bulk conductors that extend between the electrodes and the electronics package. As implantable medical devices become smaller and electrodes are included in flexible circuits, lead bodies configured in this manner may prove problematic.

SUMMARY

Various examples are described relating to neural interfaces including extensible lead bodies, systems including the same, and methods of forming the same.

In an example, a system is described. The system includes a flexible circuit defining a neural interface, the flexible circuit including an exposed electrode. The system also includes a lead body formed from a portion of the flexible circuit and including an elongate planar strand coiled about a central axis of the lead body. The elongate planar strand includes a conductive trace extending between the exposed electrode and a distal end of the elongate planar strand. The system also includes a connector assembly electrically coupled to the conductive trace via a conductive region of the elongate planar strand disposed at the distal end of the elongate planar strand. The connector assembly is configured to connect the lead body to an electronic device.

In another example, a device is described. The device includes a flexible circuit defining a neural interface. The flexible circuit includes a plurality of exposed electrodes. The device also includes a lead body formed from a portion of the flexible circuit and including a plurality of elongate planar strands. Each elongate planar strand includes a conductive trace extending between a respective exposed electrode of the plurality of exposed electrodes and a respective distal end of a respective elongate planar strand of the plurality of elongate planar strands.

In yet another example, a method is described. The method includes forming a flexible circuit that includes: an electrode region including an electrode and a lead body region including a planar strand that includes a conductive trace that extends between the electrode and a distal end of the planar strand. The method also includes manipulating the planar strand to create an extensible strand. The method also includes adding a coating to the extensible strand.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIG. 3 illustrates a top view of the example neural interface and the example extensible lead body of FIG. 2 in various states of formation, according to at least one example.

FIG. 4 illustrates a top view of the example neural interface and the example extensible lead body of FIG. 2 in various states of formation, according to at least one example.

FIG. 5 illustrates a top view of an example neural interface and an example extensible lead body in various states of formation, according to at least one example.

FIG. 6 illustrates a top view of an example neural interface and an example extensible lead body in various states of formation, according to at least one example.

FIG. 7 illustrates an example flow diagram illustrating a process of forming a neural interface and an extensible lead body, according to at least one example.

DETAILED DESCRIPTION

Examples described herein are directed to flexible circuits including neural interfaces and extensible lead bodies in the context of neurostimulation devices and/or monitoring devices. Those of ordinary skill in the art will realize that the following description is illustrative only and is not intended to be in any way limiting. For example, the flexible circuits described herein can also be used for other applications in which connections are made between electronic devices and electrodes. In some examples, the flexible circuits can be used in applications that are not implanted in human tissue. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example, a neural interface and a lead body are microfabricated from a flexible circuit. The neural interface is connected to an electronic device (e.g., neurostimulation device) via the lead body. The neural interface portion of the flexible circuit includes exposed electrodes that can be placed at different target locations in a human body. The lead body region of the flexible circuit includes elongate planar strands, with each strand including a conductive trace that is electrically coupled to one of the exposed electrodes. At an end opposite the neural interface, each elongate planar strand of the lead body can be attached to a connector assembly (e.g., a plug to mate with the electronic device). To provide extensibility of the lead body, the elongate planar strands can be coiled, braided, or otherwise wound. For example, the elongate planar strands can be coiled around a mandrel. A flexible coating (e.g., silicone polymer) can also be added to the coiled strands to provide additional extensibility and durability.

This illustrative example is given to introduce the reader to the general subject matter discussed herein and the disclosure is not limited to this example. The following sections describe various additional non-limiting examples of neural interfaces and extensible lead bodies formed from flexible circuits.

Figure 1:
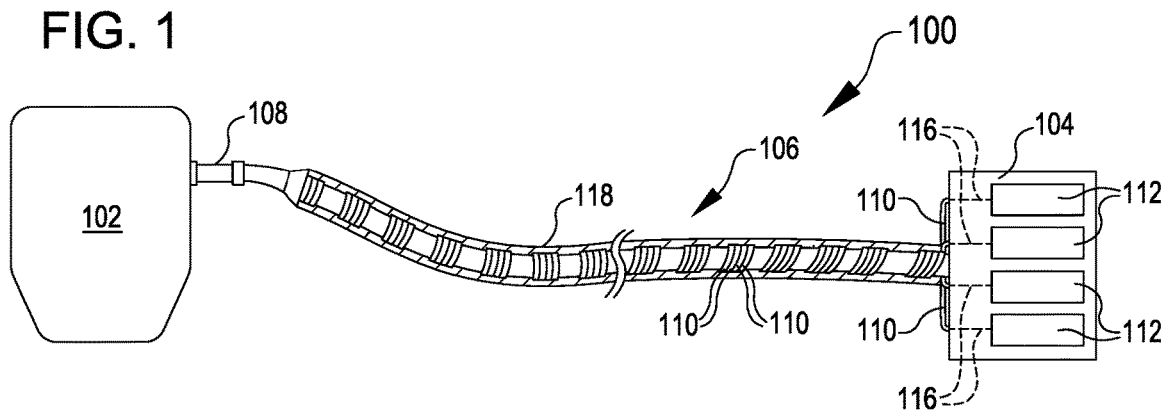
FIG. 1 illustrates a top view of a neurostimulation system, according to at least one example.

Referring now to FIG. 1, FIG. 1 illustrates a neurostimulation system 100, according to at least one example. The neurostimulation system 100 includes an electronic device 102, a neural interface 104, and a lead body 106 extending between the electronic device 102 and the neural interface 104. In some examples, the neurostimulation system 100 is implanted in a person's body through one or more incisions.

The neurostimulation system 100 also includes a connector assembly 108, which is configured to mate with the electronic device 102. As described in detail herein, the lead body 106 and the neural interface 104 are formed from as part of the same flexible circuit, with the lead body 106 including a plurality of elongate strands 110 that is coiled, braided, or otherwise wrapped in some manner so as to provide extensibility of the lead body 106.

The electronic device 102 can be any suitable active implantable device such as those for neuromodulation or neurostimulation. Examples of such devices include deep brain stimulators, cochlear implants, cardiac pacemakers, bioelectric devices, peripheral nerve stimulation systems, and other similar devices. In some examples, the electronic device 102 is a monitoring device. In this example, the electronic device 102 can be attached to the neural interface 104 in order to monitor conditions of a patient's health. Examples of such devices include those used for glucose monitoring. Such devices may also include those used for glucose monitoring and delivery.

The neural interface 104 and the elongate strands 110 are formed as a flexible circuit (e.g., flex circuit, flexible printed circuit board, flex print, and other similar flexible circuit). In some examples, the neural interface 104 and the elongate strands 110 are formed using a microfabrication technique. Thus, the neural interface 104 and the elongate strands 110 can be a flexible microfabricated circuit board. The neural interface 104 and the elongate strands 110 can be formed from polyimide, paraben, liquid crystal polymer, polyether ether ketone (PEEK), plain polyester film (PEP), or any other similar material.

The neural interface 104 includes an array of electrodes 112. Each of the electrodes 112 can be placed at one or many target locations within the patient's nerves, depending on the implementation. While the array of electrodes 112 is shown as an electrode cuff, it is understood that the electrodes 112 may take other form factors, including, for example, separate electrodes that can be spaced and placed separate from each other. The dimensions of the electrodes 112 can vary depending on the application. The neural interface 104 may also be in the geometry of a cuff around the nerves, such as a longitudinal intrafascicular interface or a transverse intrafascicular interface.

The elongate strands 110 can be formed from the same material and as part of the process as the other portions of the neural interface 104. In some examples, the neural interface 104 is formed as a single sheet including multiple layers of insulative and conductive material, and the elongate strands 110 are cut from this sheet to have the elongate form as shown and described herein.

The lead body 106 can also include a coating 118 applied over the top of the elongate strands 110. The coating 118 can be applied using one or more of a variety of processes (e.g., dip coating, cast molding, heat shrinking, and other similar processes). The coating 118 may provide additional mechanical bulk for handling and/or for abrasion resistance in vivo. The coating 118 may be formed from flexible material such as silicone polymers (e.g., medical grade silicones) and other similarly flexible materials that also have biocompatibility.

Figure 2:
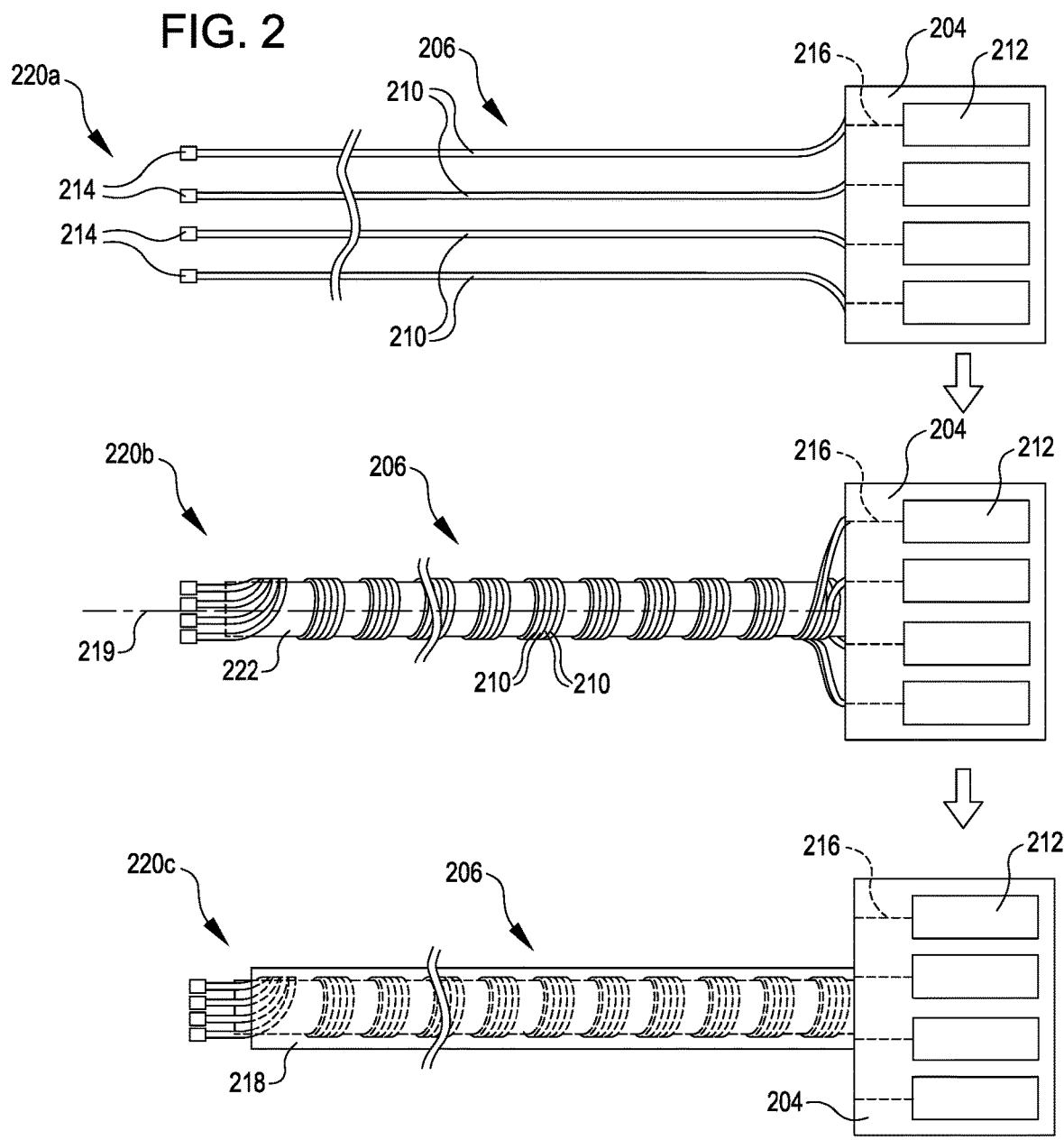
FIG. 2 illustrates a top view of an example neural interface and an example extensible lead body in various states of formation, according to at least one example.

As illustrated in FIG. 2, each elongate strand 110 includes a bond pad (e.g., a conductive region identified as bond pad 214 in FIG. 2) disposed at a distal end of the elongate strand 110. The bond pads are used to electrically couple the lead body 106 to the connector assembly 108. When included, the connector assembly 108 can be formed into a plug (e.g., a planar array of contacts, a cylindrical array of contacts, or other similar contact distribution). The connector assembly 108 can therefore interface with a corresponding socket or other interface of the electronic device 102 to detachably couple the lead body 106 with the electronic device 102. In some examples, the lead body 106 is permanently bonded to contacts on the electronic device 102 via the bond pads.

In some examples, each elongate strand 110 of the flexible circuit can be bonded to one or more microwires (e.g., a bulk conductor). The microwires can form a portion of the lead body 106 and/or can be used to connect to the connector assembly 108. Such bonding may be performed using resistance welding, conductive epoxy, thermosonic welding, mechanical crimping, laser welding, and/or any other suitable operation. For example, a mechanical connector can be used to couple an elongate strand 110 having a rectangular profile to a elongate microwire having a circular cross section. In some examples, such bonding may allow for an extensible lead body construction where the extensible region is formed from a coiled flex circuit (e.g., a coiled elongate strand 110) and a coiled microwire.

Conductive traces 116 (e.g., metal deposits held between insulative layers) extend between the exposed electrodes 112 and the bond pads. Thus, these conductive traces 116 extend within the neural interface 104 and the elongate strands 110. In some examples, each elongate strand 110 includes its own conductive trace 116. As described herein, in other examples, a single elongate strand 110 can include more than one conductive trace 116. The elongate strands 110 can have a generally rectangular cross section and can take the form of a thin flexible ribbon. In some examples, the elongate strands 110 can take some other form factor (e.g., circular cross section, non-uniform cross section, etc.).

The exposed electrodes 112, the bond pads, and the conductive traces 116 can be formed from any suitable bio-compatible conductive material such as gold, titanium, platinum, iridium, niobium, platinum alloy, iridium alloy, nickel titanium alloy, nickel-cobalt-chromium-molybdenum alloy (e.g., MP35N®), or any other suitable material.

The lead body 106 may have a length, measured from connector assembly 108 to the neural interface 104, ranging between 1 cm and 50 cm. In some examples, the length of the lead body 106 is less than 1 cm or greater than 50 cm. The lead body 106 (e.g., a combination of one or more elongate strands 110) may have a diameter ranging between 0.5 mm and 5 mm. In some examples, the diameter of the lead body 106 is less than 0.5 mm or greater than 5 mm.

The lead body 106 may also include a metallic shielding which may be installed over the top of the coating 118. The metallic shield may be formed from a metallic mesh or other flexible shielding material.

The elongate strands 110 may have curved profiles including waves oriented in one or more directions. In some examples, the elongate strands 110 have serpentine profiles. Whether curved, waved, and/or serpentine, use of elongate strands 110 arranged in this manner adds additional extensibility to the lead body 106.

The lead body 106 may be oriented perpendicular, parallel, or at any arbitrary angle compared to the neural interface 104. This may allow placement of the neural interface 204 in a manner that is compatible with the relevant anatomy.

In some examples, strain relief may be provided by molding a tapered elastomeric material from stiff regions of the lead body 106 to the flexible regions of the neural interface 104. In this manner, the tapered elastomeric material may provide strain relief at areas where stiff regions connect to flexible regions. Thus, the user of elastomeric material may be used to manage the transition from an extensible region (e.g., the lead body 106) to a non-extensible region (e.g., the connector assembly 108 and/or the neural interface 104). Such a transition zone may prevent concentration of stresses at the transition point between the two regions that might lead to mechanical failure.

FIG. 2 illustrates a top view of an example neural interface 204 and an example extensible lead body 206 in various states of formation, according to at least one example. As illustrated at state 220a, a set of elongate strands 210 is illustrated. The elongate strands 210 have been formed from the same material and as part of the same process as the neural interface 204. For example, to form the elongate strands 210, an elongate flexible circuit extending from the bond pads 214 to the distal edge of the neural interface 204 can be cut to create the elongate strands 210.

In some examples, the elongate strands 210 extend orthogonally away from the neural interface 204 along a central axis 219 of the lead body 206. In some examples, the elongate strands 210 extend away from the neural interface 204 at some other fixed angle that is less than 90 degrees and/or extend away in a curved shape. When the elongate strands 210 extend at an angle less than 90 degrees or in a curved shape, strain on the elongate strands 210 in a transition region (e.g., where the neural interface 204 transitions to the elongate strands 210) when they are coiled may be less than were they to extend at 90 degrees.

As illustrated at state 220b, the set of elongate strands 210 have been coiled around a mandrel 222 that extends along the central axis 219. The mandrel 222 is a cylindrical tube, which may be hollow or solid. When hollow, the mandrel 222 can be configured to receive a guidewire for directing and/or placing the lead body 206 and/or the neural interface 204 in a patient's body. In some examples, the mandrel 222 is removed from the lead body 206 during manufacture (e.g., after the set of elongate strands 210 have been coiled). In some examples, the mandrel 222 has a non-circular cross section (e.g., triangular, rectangular, non-uniform, etc.).

As illustrated in state 220b, the set of elongate strands 210 can be kept together as the set of elongate strands 210 coiled around the mandrel 222. In some examples, each elongate strand 210 can be coiled around the mandrel 222 with space between each elongate strand 210, or may even be coiled around the mandrel 222 so as to partially or completely overlap each other. In some examples, the elongate strands 210 are braided together instead of or in addition to coiling. For example, the elongate strands 210 can be braided as a cylindrical, helically wound braid (e.g., a biaxial braid).

The bond pads 214 can be singulated (as illustrated), or held together on a common substrate.

As illustrated in state 220c, a coating 218 can be applied to the lead body 206. For example, the coating 218 can be applied by dipping the lead body 206 into a bath of flexible material (e.g., silicone polymer). Other processes for applying the coating 218 will be discussed with reference to other figures.

FIG. 3 illustrates an example process for applying the coating 218 to the lead body 206, according to at least one example. In this example, the coating 218 is formed using a cylindrical tube 224 and a fill material 226. As illustrated at state 220c-10, the coiled elongate strands 210 and the mandrel 222 are placed into an interior of the cylindrical tube 224. As illustrated at state 220c-12, the interior of the cylindrical tube 224 is filled with the fill material 226 (e.g., a flexible coating that can be poured into, or otherwise added to, the cylindrical tube 224). This may include pouring of the fill material 226 into the cylindrical tube 224. In some examples, the mandrel 222 can be removed from the lead body 206 prior to the fill material 226 being added. Removal of the mandrel 222 may enable the elongate strands 210 to expand within the cylindrical tube 224 until the elongate strands 210 contact an interior surface of the cylindrical tube 224.

FIG. 4 illustrates an example process for applying the coating 218 to the lead body 206, according to at least one example. In this example, the coating 218 is formed using an overmold sleeve 228 and a shrink tube 230. As illustrated at state 220c-20, the overmold sleeve 228 is slide over the top of the coiled elongate strands 210 and the mandrel 222. The mandrel 222 may remain in the overmold sleeve 228 or the mandrel 222 may be removed. The overmold sleeve 228 is formed from a thermoplastic material or other suitable material. As illustrated at state 220c-22, the shrink tube 230 is slide over the top of the overmold sleeve 228. As illustrated at state 220c-24, the overmold sleeve 228 is shown inside the shrink tube 230. As illustrated at state 220c-26, heat has been applied to the shrink tube 230. Application of the heat has caused a diameter of the shrink tube 230 to contract. Application of the heat has also caused the overmold sleeve 228 to melt and reflow around the coiled elongate strands 210.

FIG. 5 illustrates a top view of an example neural interface 504 and an example extensible lead body 506 in various states of formation, according to at least one example. As illustrated at state 520a, an elongate strand 510 is provided. The elongate strand 510 has been formed from the same material and as part of the same process as a neural interface 504. For example, to form the elongate strand 510, an elongate flexible circuit extending from bond pads 514 to the distal edge of the neural interface 504 can be cut to create the elongate strand 510. A set of conductive traces 516 extend between the bond pads 514 and exposed contacts 512 of the neural interface 504. Thus, in this example, the elongate strand 510 includes multiple conductive traces 516.

As illustrated at state 520b, the elongate strand 510 has been coiled around a mandrel 522 that extends along a central axis 519 of the lead body 506. The mandrel 522 is a cylindrical tube, which may be hollow or solid. When hollow, the mandrel 522 can be configured to receive a guidewire for directing and/or placing the lead body 506 and/or neural interface 504 in a patient's body. In some examples, the mandrel 522 can be removed from the lead body 506 during manufacture (e.g., after the elongate strand 510 has been coiled).

The bond pads 514 can be held together on a common substrate (as illustrated), or singulated.

As illustrated in state 520c, a coating 518 can be applied to the lead body 506. For example, the coating 518 can be applied by dipping the lead body 506 into a bath of flexible material (e.g., silicone polymer) or using any other suitable process described herein.

FIG. 6 illustrates a top view of an example neural interface 604 and an example extensible lead body 606 in various states of formation, according to at least one example. As illustrated at state 620a, a set of elongate strands 610 is illustrated. The elongate strands 610 have been formed from the same material and as part of the same process as the neural interface 604. For example, to form the elongate strands 610, an elongate flexible circuit extending from bond pads 614 to the distal edge of the neural interface 604 can be cut to create the elongate strands 610. A set of conductive traces 616 extend between the bond pads 614 and exposed contacts 612 of the neural interface 604. Thus, in this example, each elongate strand 610 includes at least one conductive trace 516.

As illustrated at state 620b, each elongate strand 610 has been coiled around a mandrel 622 that extends along one of a set of central axes 619. The mandrels 622 are cylindrical tubes, which may be hollow or solid. When hollow, the mandrels 622 can be configured to receive guidewires for directing and/or placing the lead body 606 and/or the neural interface 604 in a patient's body. In some examples, the mandrels 622 are removed from the lead body 606 during manufacture (e.g., after the elongate strands 610 have been coiled).

The bond pads 614 can be singulated (as illustrated), or may be held together on a common substrate.

As illustrated in state 620c, a coating 618 can be applied to the lead body 606. For example, the coating 618 can be applied by dipping the individual coiled elongate strands 610 into a bath of flexible material or using any other suitable process described herein.

FIG. 7 illustrates an example flow diagram illustrating a process 700 of forming a neural interface and a lead body, according to at least one example.

The process 700 begins at 702 by forming a flexible circuit. This may include forming the flexible circuit to include an electrode region including an electrode, and a lead body region including a planar strand that includes a conductive trace that extends between the electrode and a distal end of the planar strand.

In some examples, forming the flexible circuit includes adding a first flexible sheet as a first layer of the flexible circuit. Forming the flexible circuit may also include adding conductive material as a second layer of the flexible circuit. The conductive material may form at least one of the electrode or the conductive trace. Forming the flexible circuit may also include adding a second flexible sheet as a third layer of the flexible circuit, with the second layer disposed between the first layer and the third layer. Forming the flexible circuit may also include cutting the first flexible sheet and the third flexible sheet to form the planar strand.

At 704, the process 700 includes manipulating the planar strand of the flexible circuit to create an extensible strand. In some examples, manipulating the planar strand includes coiling the planar strand about a mandrel.

In some examples, the lead body region includes a plurality of other planar strands. Manipulating the planar strand may include coiling the planar strand and the plurality of other planar strands about a mandrel.

In some examples, the lead body region includes a plurality of other planar strands. Manipulating the planar strand may include coiling the planar strand about a mandrel and coiling the plurality of other planar strands about a plurality of other mandrels.

At 706, the process 700 includes applying a coating to the extensible strand.

In some examples, applying the coating to the extensible strand includes placing the extensible strand into a cylindrical tube and adding a flexible material in a liquid form to an interior portion of the cylindrical tube.

In some examples, applying the coating to the extensible strand includes dipping the extensible strand into a flexible material in a liquid form.

In some examples, applying the coating to the extensible strand includes placing the extensible strand into a first cylindrical tube formed from a flexible material, with the extensible strand disposed within the first cylindrical. Applying the coating may also include placing the first cylindrical tube within a second cylindrical tube formed from a heat-shrink material. Applying the coating may also include applying heat to the second cylindrical tube to cause the flexible material to melt.

In the following, further examples are described to facilitate the understanding of the present disclosure.

Example 1

In this example, there is provided a system, including:

a flexible circuit defining a neural interface, the flexible circuit including an exposed electrode;

a lead body formed from a portion of the flexible circuit and including an elongate planar strand coiled about a central axis of the lead body, the elongate planar strand including a conductive trace extending between the exposed electrode and a distal end of the elongate planar strand; and a connector assembly electrically coupled to the conductive trace via a conductive region of the elongate planar strand disposed at the distal end of the elongate planar strand, the connector assembly configured to connect the lead body to an electronic device.

Example 2

In this example, there is provided a system of any of the preceding or subsequent examples, wherein the electronic device is configured to receive first electrical signals from the exposed electrode via the conductive trace and/or to send second electrical signals to the exposed electrode via the conductive trace.

Example 3

In this example, there is provided a system of any of the preceding or subsequent examples, wherein the elongate planar strand is one of a plurality of elongate planar strands, each elongate planar strand of the plurality of elongate planar strands including a respective conductive trace.

Example 4

In this example, there is provided a system of any of the preceding or subsequent examples, wherein each elongate planar strand of the plurality of elongate planar strands is coiled about a single mandrel.

Example 5

In this example, there is provided a system of any of the preceding or subsequent examples, wherein each elongate planar strand of the plurality of elongate planar strands is coiled about its own respective mandrel.

Example 6

In this example, there is provided a system of any of the preceding or subsequent examples, wherein the lead body includes a flexible coating.

Example 7

In this example, there is provided a system of any of the preceding or subsequent examples, wherein the flexible coating is formed using a cast molding technique, a dip coating technique, or a heat-shrinking technique.

Example 8

In this example, there is provided a device, including:
a flexible circuit defining a neural interface, the flexible circuit including a plurality of exposed electrodes; and
a lead body formed from a portion of the flexible circuit and including a plurality of elongate planar strands, each elongate planar strand including a conductive trace extending between a respective exposed electrode of the plurality of exposed electrodes and a respective distal end of a respective elongate planar strand of the plurality of elongate planar strands.

Example 9

In this example, there is provided a device of any of the preceding or subsequent examples, further including a connector assembly attached to the lead body at the respective distal ends of the plurality of elongate planar strands, the connector assembly being electrically coupled to the plurality of exposed electrodes via the respective conductive traces.

Example 10

In this example, there is provided a device of any of the preceding or subsequent examples, wherein each elongate planar strand of the plurality of elongate planar strands is coiled about a central axis of the lead body.

Example 11

In this example, there is provided a device of any of the preceding or subsequent examples, wherein each elongate planar strand of the plurality of elongate planar strands is coiled about its own central axis.

Example 12

In this example, there is provided a device of any of the preceding or subsequent examples, wherein the plurality of other elongate planar strands are braided together.

Example 13

In this example, there is provided a device of any of the preceding or subsequent examples, wherein the lead body includes a bond pad region disposed at a lead body distal end, the respective conductive traces extending between the bond pad region and the plurality of exposed electrodes.

Example 14

In this example, there is provided a device of any of the preceding or subsequent examples, wherein a first elongate planar strand of the plurality of elongate planar strands includes a pair of conductive traces extending between a pair of exposed electrodes of the plurality of exposed electrodes and a first distal end of the first elongate strand.

Example 15

In this example, there is provided a device of any of the preceding or subsequent examples, further including a plurality of mandrels, and wherein each elongate planar strand of the plurality of elongate planar strands is coiled about a respective mandrel of the plurality of mandrels.

Example 16

In this example, there is provided a device of any of the preceding or subsequent examples, wherein at least one mandrel of the plurality of mandrels is a cylindrical tube defining a hollow interior.

Example 17

In this example, there is provided a device of any of the preceding or subsequent examples, wherein at least one elongate planar strand of the plurality of elongate planar strands is formed to include a plurality of waves oriented with respect to a planar top surface of the at least one elongate planar strand.

Example 18

In this example, there is provided a device of any of the preceding or subsequent examples, wherein the lead body includes a flexible coating.

Example 19

In this example, there is provided a method, including:
forming a flexible circuit that includes:
an electrode region including an electrode; and
a lead body region including a planar strand that includes
 a conductive trace that extends between the electrode and a distal end of the planar strand;
manipulating the planar strand to create an extensible strand; and
adding a coating to the extensible strand Example 20

In this example, there is provided a method of any of the preceding or subsequent examples, wherein manipulating the planar strand includes coiling the planar strand about a mandrel.

Example 21

In this example, there is provided a method of any of the preceding or subsequent examples, wherein the lead body region includes a plurality of other planar strands, and wherein manipulating the planar strand includes coiling the planar strand and the plurality of other planar strands about a mandrel.

Example 22

In this example, there is provided a method of any of the preceding or subsequent examples, wherein the lead body region includes a plurality of other planar strands, and wherein manipulating the planar strand includes coiling the planar strand about a mandrel and coiling the plurality of other planar strands about a plurality of other mandrels.

Example 23

In this example, there is provided a method of any of the preceding or subsequent examples, wherein the lead body region includes a plurality of other planar strands, and wherein manipulating the planar strand includes braiding the planar strand and the plurality of other planar strands together.

Example 24

In this example, there is provided a method of any of the preceding or subsequent examples, wherein forming the flexible circuit includes:
adding a first flexible sheet as a first layer of the flexible circuit;
adding conductive material as a second layer of the flexible circuit, the conductive material forming the electrode and/or the conductive trace;
adding a second flexible sheet as a third layer of the flexible circuit, with the second layer disposed between the first layer and the third layer; and
cutting the first flexible sheet and the third flexible sheet to form the planar strand.

Example 25

In this example, there is provided a method of any of the preceding or subsequent examples, wherein adding the coating to the extensible strand includes:
placing the extensible strand into a cylindrical tube; and
adding a flexible material in a liquid form to an interior portion of the cylindrical tube.

Example 26

In this example, there is provided a method of any of the preceding or subsequent examples, wherein adding the coating to the extensible strand includes dipping the extensible strand into a flexible material in a liquid form.

Example 27

In this example, there is provided a method of any of the preceding or subsequent examples, wherein adding the coating to the extensible strand includes:
placing the extensible strand into a first cylindrical tube formed from a flexible material;
with the extensible strand disposed within the first cylindrical, placing the first cylindrical tube within a second cylindrical tube formed from a heat-shrink material; and
applying heat to the second cylindrical tube to cause the flexible material to melt.

Example 28

In this example, there is provided a method of any of the preceding or subsequent examples, further comprising adding a elastomeric material that extends from a first portion of the electrode region to a second portion of the lead body region.

Example 29

In this example, there is provided a method of any of the preceding or subsequent examples, further comprising mechanically and electrically connecting the elongate planar strand and a connector assembly using at least one of mechanical crimping, mechanical crimping in connection with elevated temperature, or mechanical crimping in connection with ultrasonic energy.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

What is claimed is:
1. A system, comprising:
a flexible circuit defining a neural interface, the flexible circuit comprising an exposed electrode;
a lead body formed from a portion of the flexible circuit and comprising an elongate planar strand coiled about a central axis of the lead body, the elongate planar strand comprising a conductive trace extending between the exposed electrode and a distal end of the elongate planar strand; and
a connector assembly electrically coupled to the conductive trace via a conductive region of the elongate planar strand disposed at the distal end of the elongate planar strand, the connector assembly configured to connect the lead body to an electronic device.

2. The system of claim 1, wherein the electronic device is configured to receive first electrical signals from the exposed electrode via the conductive trace and/or to send second electrical signals to the exposed electrode via the conductive trace.

3. The system of claim 1, wherein the elongate planar strand is one of a plurality of elongate planar strands, each elongate planar strand of the plurality of elongate planar strands comprising a respective conductive trace.

4. The system of claim 3, wherein each elongate planar strand of the plurality of elongate planar strands is coiled about a single mandrel.

5. The system of claim 3, wherein each elongate planar strand of the plurality of elongate planar strands is coiled about its own respective mandrel.

6. The system of claim 1, wherein the lead body comprises a flexible coating.

7. The system of claim 6, wherein the flexible coating is formed using a cast molding technique, a dip coating technique, or a heat-shrinking technique.

8. A device, comprising:
a flexible circuit defining a neural interface, the flexible circuit comprising a plurality of exposed electrodes; and
a lead body formed from a portion of the flexible circuit and comprising a plurality of elongate planar strands, each elongate planar strand comprising a conductive trace extending between a respective exposed electrode of the plurality of exposed electrodes and a respective distal end of a respective elongate planar strand of the plurality of elongate planar strands.

9. The device of claim 8, further comprising a connector assembly attached to the lead body at the respective distal ends of the plurality of elongate planar strands, the connector assembly being electrically coupled to the plurality of exposed electrodes via the respective conductive traces.

10. The device of claim 8, wherein each elongate planar strand of the plurality of elongate planar strands is coiled about a central axis of the lead body.

11. The device of claim 8, wherein each elongate planar strand of the plurality of elongate planar strands is coiled about its own central axis.

12. The device of claim 8, wherein the plurality of elongate planar strands is braided together.

13. The device of claim 8, wherein the lead body comprises a bond pad region disposed at a lead body distal end, the respective conductive traces extending between the bond pad region and the plurality of exposed electrodes.

14. The device of claim 8, wherein a first elongate planar strand of the plurality of elongate planar strands comprises a pair of conductive traces extending between a pair of exposed electrodes of the plurality of exposed electrodes and a first distal end of the first elongate planar strand.

15. The device of claim 8, further comprising a plurality of mandrels, and wherein each elongate planar strand of the plurality of elongate planar strands is coiled about a respective mandrel of the plurality of mandrels.

16. The device of claim 15, wherein at least one mandrel of the plurality of mandrels is a cylindrical tube defining a hollow interior.

17. The device of claim 8, wherein at least one elongate planar strand of the plurality of elongate planar strands is formed to include a plurality of waves oriented with respect to a planar top surface of the at least one elongate planar strand.

18. The device of claim 8, wherein the lead body comprises a flexible coating.

19. A method, comprising:
forming a flexible circuit that includes:
an electrode region comprising an electrode; and
a lead body region comprising a planar strand that includes a conductive trace that extends between the electrode and a distal end of the planar strand;
manipulating the planar strand to create an extensible strand; and
adding a coating to the extensible strand.

20. The method of claim 19, wherein manipulating the planar strand comprises coiling the planar strand about a mandrel.

21. The method of claim 19, wherein the lead body region comprises a plurality of other planar strands, and wherein manipulating the planar strand comprises coiling the planar strand and the plurality of other planar strands about a mandrel.

22. The method of claim 19, wherein the lead body region comprises a plurality of other planar strands, and wherein manipulating the planar strand comprises coiling the planar strand about a mandrel and coiling the plurality of other planar strands about a plurality of other mandrels.

23. The method of claim 19, wherein the lead body region comprises a plurality of other planar strands, and wherein manipulating the planar strand comprises braiding the planar strand and the plurality of other planar strands together.

24. The method of claim 19, wherein forming the flexible circuit comprises:
adding a first flexible sheet as a first layer of the flexible circuit;
adding conductive material as a second layer of the flexible circuit, the conductive material forming the electrode and/or the conductive trace;
adding a second flexible sheet as a third layer of the flexible circuit, with the second layer disposed between the first layer and the third layer; and
cutting the first flexible sheet and the second flexible sheet to form the planar strand.

25. The method of claim 19, wherein adding the coating to the extensible strand comprises:
placing the extensible strand into a cylindrical tube; and
adding a flexible material in a liquid form to an interior portion of the cylindrical tube.

26. The method of claim 19, wherein adding the coating to the extensible strand comprises dipping the extensible strand into a flexible material in a liquid form.

27. The method of claim 19, wherein adding the coating to the extensible strand comprises:
placing the extensible strand into a first cylindrical tube formed from a flexible material;
with the extensible strand disposed within the first cylindrical tube, placing the first cylindrical tube within a second cylindrical tube formed from a heat-shrink material; and
applying heat to the second cylindrical tube to cause the flexible material to melt.

28. The method of claim 19, further comprising adding a elastomeric material that extends from a first portion of the electrode region to a second portion of the lead body region.

29. The method of claim 19, further comprising mechanically and electrically connecting the planar strand and a connector assembly using at least one of mechanical crimping, mechanical crimping in connection with elevated temperature, or mechanical crimping in connection with ultrasonic energy.

* * * * *